United States Patent [19]

Burgmeier

[11] Patent Number: 5,769,817
[45] Date of Patent: Jun. 23, 1998

[54] COEXTRUDED BALLOON AND METHOD OF MAKING SAME

[75] Inventor: Robert E. Burgmeier, Plymouth, Minn.

[73] Assignee: Schneider (USA) Inc., Minneapolis, Minn.

[21] Appl. No.: 810,162

[22] Filed: Feb. 28, 1997

[51] Int. Cl.$^6$ ................................................ A61M 29/00
[52] U.S. Cl. ............................... 604/96; 604/49; 606/194
[58] Field of Search ............................ 604/96, 101, 102, 604/103, 49, 264, 280, 53; 606/192, 193, 194, 198, 108

[56] References Cited

U.S. PATENT DOCUMENTS

| Re. 33,561 | 3/1991 | Levy . |
| 5,041,089 | 8/1991 | Mueller et al. . |
| 5,087,394 | 2/1992 | Keith . |
| 5,195,969 | 3/1993 | Wang et al. . |
| 5,290,306 | 3/1994 | Trotta et al. . |
| 5,342,305 | 8/1994 | Shonk . |
| 5,344,400 | 9/1994 | Kaneko et al. . |
| 5,344,401 | 9/1994 | Radisch et al. . |
| 5,358,486 | 10/1994 | Saab . |
| 5,403,280 | 4/1995 | Wang . |
| 5,403,340 | 4/1995 | Wang et al. . |
| 5,409,495 | 4/1995 | Osborn . |
| 5,447,497 | 9/1995 | Sogard et al. . |
| 5,478,320 | 12/1995 | Trotta . |
| 5,490,839 | 2/1996 | Wang et al. . |
| 5,556,383 | 9/1996 | Wang et al. . |

FOREIGN PATENT DOCUMENTS

| 274411 | 7/1988 | European Pat. Off. . |
| 420488 | 4/1991 | European Pat. Off. . |
| 540858 | 5/1993 | European Pat. Off. . |
| WO9509667 | 4/1995 | WIPO . |

*Primary Examiner*—John D. Yasko
*Attorney, Agent, or Firm*—Haugen and Nikolai, P.A.

[57] ABSTRACT

An expander member for a balloon catheter to be used in stent delivery applications comprises a double-walled tubular member that is adapted for attachment to a distal end portion of an elongated, flexible, tubular catheter body. The outer wall is preferably a polyamide, such as Nylon-12, and the inner wall is PET. By properly controlling the percentage of the polyamide relative to the PET content, the distension characteristics of the resulting expander member can be tailored to fall in a range less than 15 percent. The outer Nylon-12 layer provides the expander member with high abrasion resistance. By appropriately temperature annealing the expander member, any tendency toward winging upon deflation thereof is reduced.

12 Claims, 3 Drawing Sheets

COEXTRUDED BALLOON AND METHOD OF MAKING SAME

BACKGROUND OF THE INVENTION

I. Field of the Invention

This invention relates generally to methods for manufacturing the balloon element for balloon catheters, and more particularly to such a balloon featuring high burst strength, high abrasion resistance and a compliance in a range of about 13 percent or less, making such a balloon highly suitable for use on stent delivery catheters.

II. Discussion of the Prior Art

In treating patients with cardiovascular disease, it is now quite common to perform percutaneous transluminal angioplasty procedures for the purpose of restoring greater patency to a previously occluded blood vessel. In carrying out this procedure, a balloon angioplasty catheter is introduced at a point in the vascular system, such as the femoral artery, and then is advanced through the vascular system until an uninflated balloon or expander member on the distal end of the catheter is positioned across a stenosis to be treated. Once so positioned, an inflation fluid is injected under pressure through a lumen in the catheter body to inflate and thereby expand the balloon member on the distal end of the catheter to a relatively high pressure. The resulting expansion of the balloon member has the effect of compressing the stenotic lesion into the vessel wall.

In other cases, an atherectomy catheter may be introduced and advanced through the vascular system and a suitable cutting instrument carried on the distal end of that catheter is then deployed and used to cut through the fatty deposits comprising the stenotic lesion with the resulting debris being aspirated back through the catheter.

In carrying out either of these procedures, it is possible that the vessel wall at the site of the lesion may be torn or weakened so as to no longer be self-supporting. In this event, the practice has been to introduce a stent to add mechanical support to the blood vessel. Such stents are typically deployed utilizing a balloon catheter. Specifically, with the balloon or expander member uninflated and closely conforming to the catheter body on which it is mounted, a tubular stent member is positioned over the balloon in concentric fashion. The catheter carrying the stent is then advanced through the vascular system until the stent is in a position to bridge the weakened area of the blood vessel that had previously been treated. Once so positioned, an inflation fluid is injected through the catheter to inflate the expander member and thereby expand and plastically deform the stent to a predetermined outer diameter in the expanded condition so as to engage the vessel wall. The balloon is then deflated by aspirating the inflation fluid from the balloon, allowing the catheter carrying the balloon to be withdrawn, leaving the expanded stent in place.

Self-expanding stents, such as the stent disclosed in U.S. Pat. No. 4,655,771, may also be deployed in conjunction with an expander member. For instance, following self-expansion in a vessel, a balloon can be inserted in the self-expanding stent and inflated to push the stent firmly against the vessel wall.

It is important that a stent delivery catheter have a balloon member that is semi-compliant, that has high abrasion resistance, high hoop strength and burst resistance and a memory property that allows the once expanded stent to be collapsed so as to conform to the outside surface of the catheter body with a minimum of winging.

Control over the compliance characteristic can be achieved through proper selection of (1) the plastic materials used in fabricating the balloon, (2) the wall thickness of the balloon and (3) the extent to which the material comprising the balloon is oriented during its formation. For example, if a highly non-compliant balloon is desired, highly orientable polymers, such as polyethylene terephthalate (PET), polypropylene polycarbonates or Nylon are good candidates. More highly compliant balloons result when thermoplastic materials, such as polyethylene and various copolymers and blends of polyethylene, ionomers, polyesters, polyamides and polyvinyl chloride, are employed in creating the parison from which the balloon is formed in a stretch blow-molding operation.

Where a desired balance of physical properties, such as distensibility, abrasion resistance, bondability, etc., cannot be achieved using a single material or blend of materials in forming a balloon, it is also known in the art to coextrude two or more different materials as described in U.S. Pat. No. 5,270,086 to Hamlin and in published PCT application WO95/09667. The Wang et al. U.S. Pat. No. 5,195,969 describes a medical balloon for an angioplasty catheter that comprises a coextrusion of Nylon-12 or PET with polyethylene where the Nylon-12 or PET provides high hoop strength and the polyethylene layer enhances the bondability of the balloon to the catheter on which it is affixed.

Missing from the prior art, however, is a teaching of a method for fabricating a balloon structure tailored to meet the requirements necessary for use in stent delivery, i.e., a balloon possessing high abrasion resistance to withstand the frictional effects of the balloon rubbing against the stent as expansion of the stent takes place, controlled distensibility to preclude over expansion of the stent relative to the blood vessel, a high burst strength and rewrappability.

SUMMARY OF THE INVENTION

It is a purpose of the present invention to provide a balloon for high pressure stent expansion. Such a balloon has been achieved by coextrusion of a PET, and polyamide (Nylon-12) where the Nylon-12 comprises the outer layer and PET comprises the innermost layer. It has been found that by controlling the percent-by-weight concentration of Nylon to that of the PET, it is possible to tailor the compliance characteristics of the resulting balloon so as to reside in a range from about 5–15 percent when experiencing pressure changes from 8 atmospheres to 18 atmospheres, preferably from about 7–13 percent. In that the burst pressure is above 25 atmospheres, an adequate margin of safety is readily realized.

The balloon itself comprises an expansible, double-walled tubular member adapted for attachment at opposed ends thereof to a distal end portion of an elongated, flexible catheter. When the balloon is bonded to the outer wall of the tubular catheter, an interior chamber is defined. The catheter includes an inflation lumen extending its length, and it is in fluid communication with the interior chamber of the double-walled tubular member. The outermost wall of the double-walled tubular member is polyamide, such as Nylon-12, and the inner wall is PET. By controlling the percentage-by-weight of the polyamide so as to be in a range of from 20–80 percent with the balance being PET, the double-walled tubular member exhibits a compliance factor of about 13 percent or less over a pressure range from 8 atmospheres to 18 atmospheres. The coextruded double-walled structure with polyamide comprising the outermost layer provides a way to increase the abrasion resistance of a PET balloon without significantly lowering the burst pressure of the balloon.

To improve the rewrap characteristics of the resulting balloon, it may be temperature annealed in a fashion set out in copending application of Suranjan Roychowdhury, Ser. No. 08/625,495, filed Apr. 1, 1996. Experiments have shown that by varying the Nylon content relative to the PET content and/or the annealing temperatures, desired properties for a stent delivery catheter can be achieved.

DESCRIPTION OF THE DRAWINGS

The foregoing features, objects and advantages of the invention will become apparent to those skilled in the art from the following detailed description of a preferred embodiment, especially when considered in conjunction with the accompanying drawing in which.

DESCRIPTION OF THE PREFERRED EMBODIMENT

Figure 2:
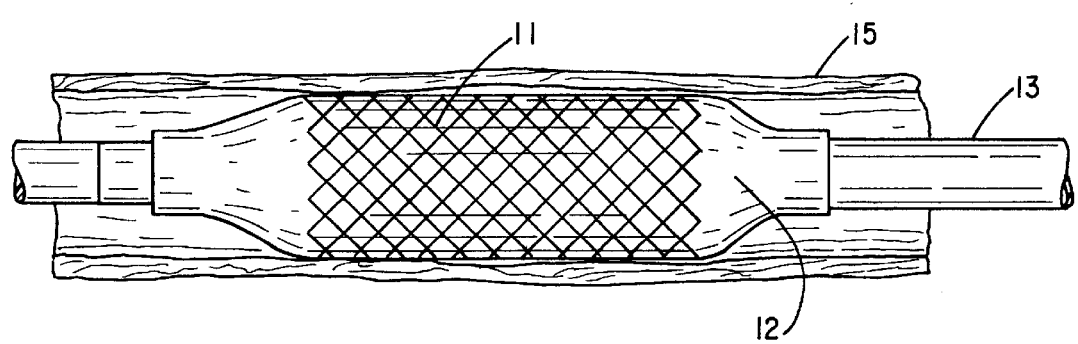
FIG. 2 is similar to FIG. 1 but also shows a stent disposed on the delivery catheter.

Referring to the drawing, there is shown the distal end portion of a stent delivery catheter indicated generally by numeral 10. The stent 11 itself (FIG. 2) may typically comprise a braided or slotted, non-self-expanding metal or plastic tube whose inside diameter closely conforms to the exterior of the expander member 12 when the expander member is non-inflated (not shown). The delivery catheter 13 may be introduced into the vascular system 15 in a conventional way and then advanced through the vascular system until the expander member 12 on the catheter body stock 14 carrying the yet non-expanded stent is juxtaposed relative to a treatment site in the vascular system. Once so positioned, the expander member 12 is inflated and, in doing so, the stent is also expanded to a predetermined diameter that is a function of the outside diameter of the expander member 12 at a desired pressure.

Once the stent has been expanded in the manner described, the expander member 12 is again deflated by aspirating the inflation fluid therefrom and, once deflated, is extracted from the vascular system.

It is, of course, desirable that upon aspiration, the expander member 12 deflates so as to closely conform to the outside diameter of the catheter body stock 14 on which it is mounted. So-called winging or pancaking of the expander member is undesirable. Furthermore, when the end-use of the balloon catheter is for deploying non-self-expanding stents, it is important that the expander member 12 possess high abrasion resistance so as to prevent rupture as the surface of the expander member 12 frictionally engages the stent during expansion thereof.

Figure 1:
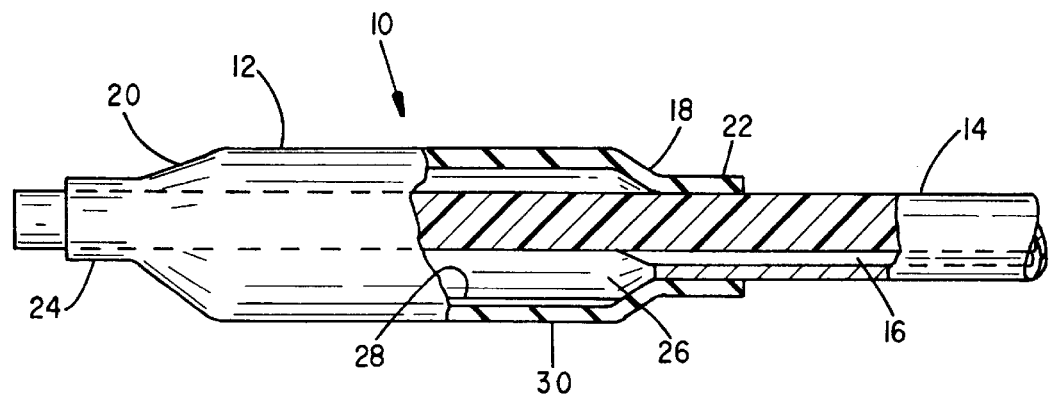
FIG. 1 is a greatly enlarged, partially sectioned side elevation view of a distal end portion of a stent delivery catheter constructed in accordance with the teachings of the present invention.

As shown in FIG. 1, the catheter body stock 14 comprises an elongated, flexible tube having an inflation lumen 16 extending the length thereof. Affixed to the distal end portion of the catheter body stock 14 is a generally cylindrical, tubular expander member having conically-shaped end portions as at 18 and 20 which are bonded to the exterior wall of the catheter body stock 14 in zones 22 and 24 to define a hollow chamber 26 when the expander member 12 is inflated. The distal end of the inflation lumen 16 extends beyond the seal zone 22 permitting inflation fluid under pressure to flow into the chamber 26 and expand the expander member.

In accordance with the present invention, the expander member 12 is formed by blow-molding and stretching a parison previously formed in a coextrusion process such as is described in the Hamlin U.S. Pat. No. 5,270,086. Thus, the resulting expander member 12 has double walls 28 and 30, respectively. The coextruded parison is designed to have an inner wall comprising PET and an outer wall of polyamide, with Nylon-12 being preferred. Several nylons suitable for the expander member are Grilamid L25, EMS, Vestamide 2101 F, HULS and Vestamide 1801 F, HULS. The PET component may be ICI 5822 C or Shell Traytuf 1006.

When subjected to the stretch/blow-molding operation, both the PET layer and the Nylon layer are biaxially oriented within a heated mold until a desired composite wall thickness and outer diameter are attained. Typical wall thickness in an unexpanded state may range from about 0.0004–0.0009, preferably about 0.00045–0.0006 inches.

When the end-use of the balloon catheter is stent delivery, it is important that the expander member 12 exhibit a relatively low compliance factor so that the stent will only be expanded to a desired outside diameter. Those skilled in the art will recognize that if the expander member is highly compliant, it becomes more difficult to control the extent of expansion of the stent being delivered thereby. It has been determined that if the compliance factor is kept below about 15 percent, and preferably 13 percent or less for pressures in the range of from 18 atmospheres to 18 atmospheres, good control over expanded stent diameter can be realized.

It has been determined that when the outer wall 30 of the expander member 12 comprises polyamide, such as Nylon-12, and when the inner wall 28 is PET, of the percent by weight of the polyamide in the composite is in the range of from 20 to 80 percent, the balloon's compliance can be maintained in the desired range indicated. The PET layer 28 provides an expander member with a high burst strength while the outer Nylon-12 layer 30 offers excellent abrasion resistance.

To improve the conformance parameter of the composite, double-walled expander member, such that upon inflation and subsequent deflation, it conforms closely to the profile of the catheter body stock 14, temperature annealing of the expander member in accordance with the teachings of the aforereferenced Roychowdhury patent application may be used. Preferably, a blown expander member is taco-wrapped in a sheath and subjected to a heating cycle at a temperature between 75° and 95° C. for a period of time in the range of from 1 to 4 hours. The annealed double-walled balloon has been found to closely conform to the outer diameter of the catheter body stock 14 when first expanded to a pressure of about 8 atmospheres and subsequently deflated by aspirating the inflation fluid from the chamber 26. No appreciable winging results.

It has also been found that the distension curve for the composite, double-walled balloon can be tailored based upon the Nylon-12 content and the annealing conditions imposed.

EXAMPLE

An expander member having a diameter of 3.0 mm and comprising coextruded PET, and Nylon-12 in ratios from about 55–45 to 65–35 were formed and during the stretch/blow-molding thereof were stretched a distance of from 5:1 to 8:1 in the radial direction. The expander members exhibited a wall thickness in the range of from 0.0005 to 0.001 inches and in an unexpanded state and were found to exhibit the following composite hoop stresses and burst pressures for the indicated wall thicknesses. Hoop stress was calculated as a σ=PD/2t, wherein t is the balloon wall thickness measured in an unexpanded state, P is the burst pressure measured at 37° C., and D is the diameter at 10 atmospheres and room temperature.

| Wall (in.) | Nylon (%) | Burst (psi) | Hoop Stress (psi) |
|---|---|---|---|
| .00058 | 38.2 | 441.8 | 44,941 |
| .0007 | 38.5 | 436.4 | 36,782 |
| .0009 | 41.7 | 483.0 | 35,621 |

Figure 3A:
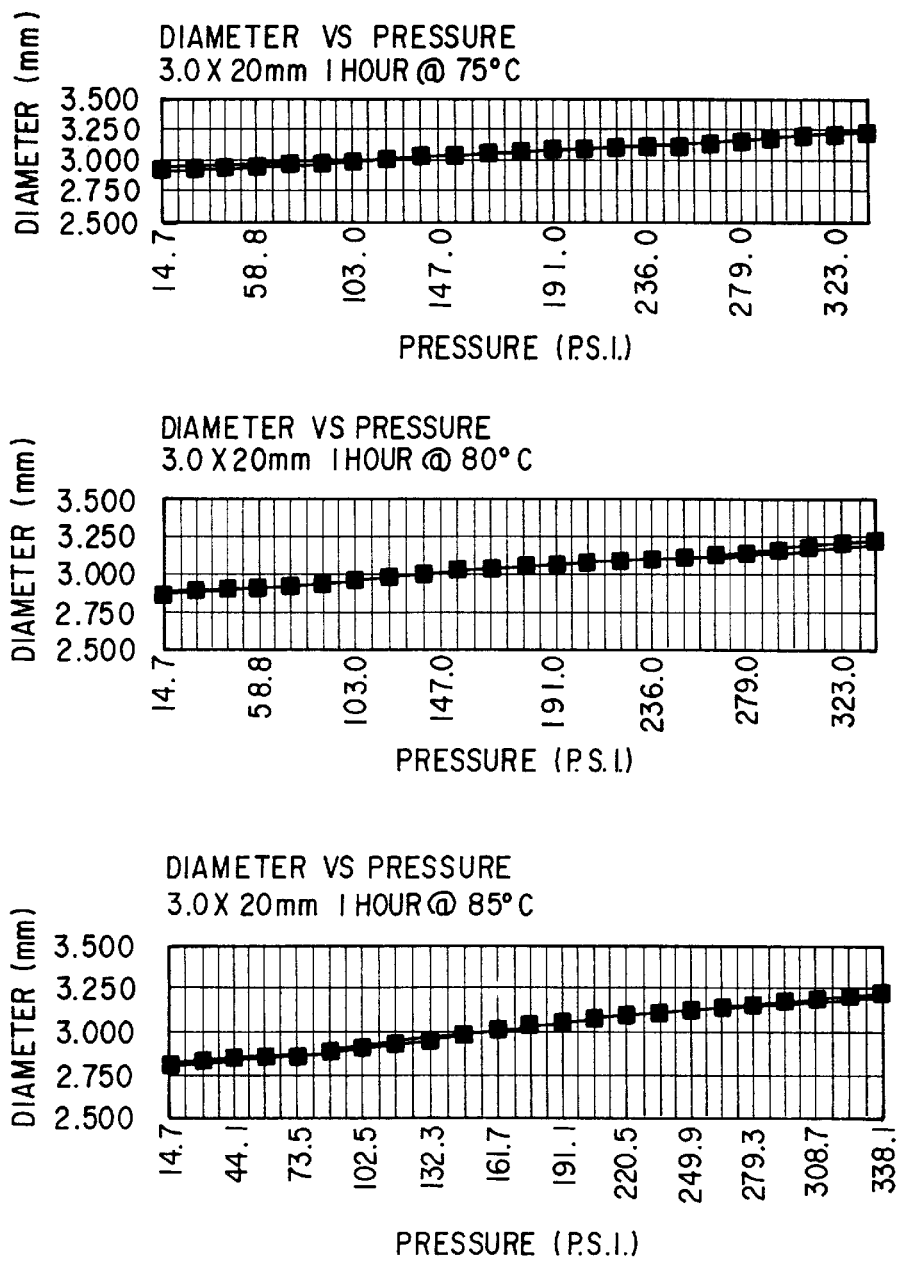
FIGS. 3A and 3B are graphs showing variation of the compliance characteristics of coextruded PET/Nylon expander members with annealing temperatures.
Figure 3B:
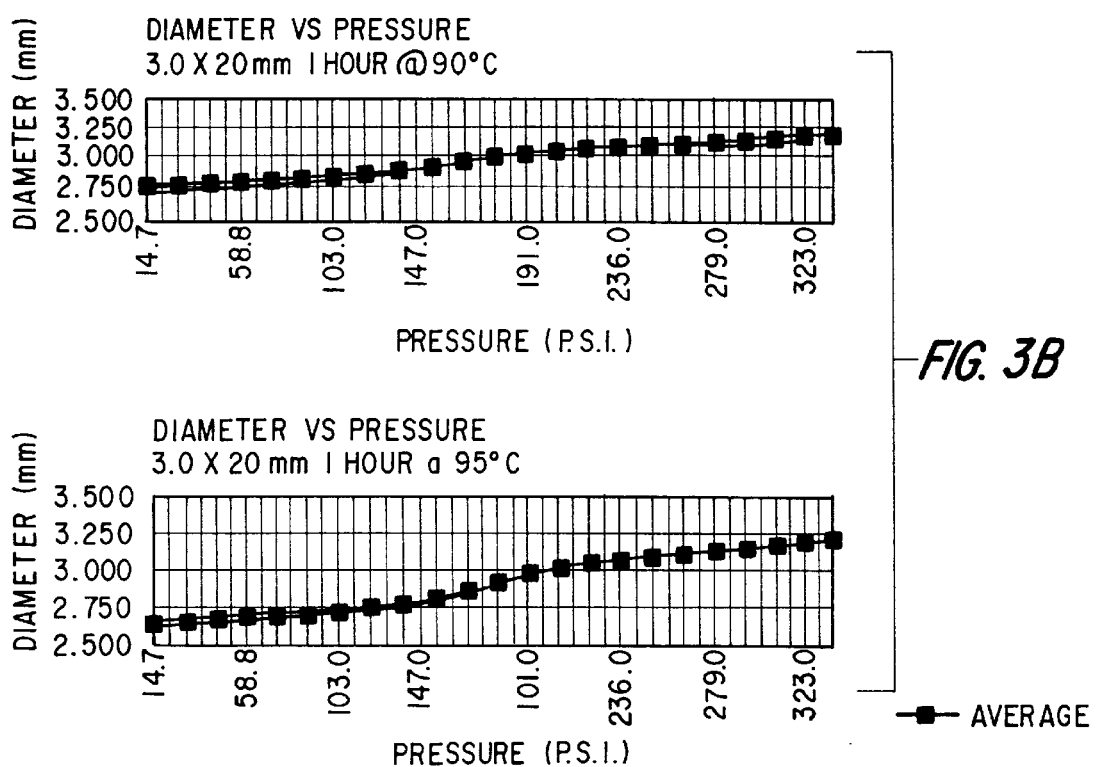

FIGS. 3A and 3B are graphs reflecting the variation in the compliance characteristics of average value for five groups of five samples each of catheter expander members when each group of five was subjected to annealing temperatures varying from 75° for the first group to 95° C. for the fifth group in each case for one hour. The expander members were each 3.0 mm in diameter and 20 mm in length. They comprised 40% Nylon, 60% PET coextrusions. These curves show that by proper control of annealing temperatures, it is possible to tailor the expander members to exhibit desired compliance characteristics in a range of from 10% to 18% between 8 and 18 atmospheres. The relative percentages of Nylon and PET in the co-extrusion also has an effect on the compliance characteristics. Measurements were taken at room temperature and using water as the inflation medium. A summary of the results is shown in Table 1 below.

modifications, both as to the equipment details and operating procedures, can be accomplished without departing from the scope of the invention itself.

What is claimed is:

1. An inflatable expander member for a balloon catheter, comprising:

(a) an expansible, double walled tubular member adapted for attachment to a distal end portion of an elongated, flexible catheter body, an outermost wall of the double walled tubular member being polyamide and an inner wall of the double walled tubular member being polyethylene terephthalate, where the percentage by weight of polyamide is in a range of from 20 to 80 percent and with the balance being polyethylene terephthalate, the double walled tubular member exhibiting a compliance factor of about 13 percent or less over a pressure range of from 8 atmospheres to 18 atmospheres.

2. The expander member as in claim 1 wherein the polyamide is Nylon-12.

3. The expander member as in claim 1 wherein the burst strength of the double walled tubular member is in excess of 25 atmospheres.

4. The expander member as in claim 1 wherein the double walled tubular member has a generally cylindrical central portion with generally conical end portions.

5. A balloon catheter comprising:

(a) an elongated flexible tubular member having a proximal end, a distal end and a lumen for delivery of an inflation fluid;

(b) an expansible, double walled tubular member adapted for attachment to a distal end portion of an elongated,

TABLE I

| 1 hour @ 75° C. | | 1 hour @ 80° C. | | 1 hour @ 85° C. | | 1 hour @ 90° C. | | 1 hour @ 95° C. | |
|---|---|---|---|---|---|---|---|---|---|
| PSI | Average | PSI | Average | PSI | Average | PSI | Average | PSI | Average |
| 14.7 | 2.921 | 14.7 | 2.879 | 14.7 | 2.805 | 14.7 | 2.754 | 14.7 | 2.649 |
| 29.4 | 2.935 | 29.4 | 2.893 | 29.4 | 2.827 | 29.4 | 2.783 | 29.4 | 2.672 |
| 44.1 | 2.946 | 44.1 | 2.905 | 44.1 | 2.847 | 44.1 | 2.797 | 44.1 | 2.687 |
| 58.8 | 2.953 | 58.8 | 2.915 | 58.8 | 2.861 | 58.8 | 2.809 | 58.8 | 2.698 |
| 73.5 | 2.960 | 73.5 | 2.925 | 73.5 | 2.864 | 73.5 | 2.821 | 73.5 | 2.710 |
| 88.2 | 2.970 | 88.2 | 2.939 | 88.2 | 2.886 | 88.2 | 2.830 | 88.2 | 2.719 |
| 102.5 | 2.982 | 102.5 | 2.956 | 102.5 | 2.902 | 102.5 | 2.850 | 102.5 | 2.732 |
| 117.6 | 2.996 | 117.6 | 2.976 | 117.6 | 2.916 | 117.6 | 2.864 | 117.6 | 2.748 |
| 132.3 | 3.013 | 132.3 | 2.997 | 132.3 | 2.937 | 132.3 | 2.892 | 132.3 | 2.769 |
| 147.0 | 3.029 | 147.0 | 3.018 | 147.0 | 2.967 | 147.0 | 2.923 | 147.0 | 2.806 |
| 161.7 | 3.042 | 161.7 | 3.034 | 161.7 | 2.996 | 161.7 | 2968 | 161.7 | 2.857 |
| 176.4 | 3.056 | 176.4 | 3.047 | 176.4 | 3.022 | 176.4 | 3.002 | 176.4 | 2.919 |
| 191.1 | 3.069 | 191.1 | 3.061 | 191.1 | 3.046 | 191.1 | 3.036 | 191.1 | 2.978 |
| 205.8 | 3.082 | 205.8 | 3.079 | 205.8 | 3.065 | 205.8 | 3.061 | 205.8 | 3.019 |
| 220.5 | 3.101 | 220.5 | 3.089 | 220.5 | 3.065 | 220.5 | 3.079 | 220.5 | 3.054 |
| 235.8 | 3.116 | 235.8 | 3.104 | 235.8 | 3.101 | 235.8 | 3.095 | 235.8 | 3.079 |
| 249.9 | 3.132 | 249.9 | 3.118 | 249.9 | 3.118 | 249.9 | 3.115 | 249.9 | 3.104 |
| 264.6 | 3.153 | 264.6 | 3.135 | 264.6 | 3.138 | 264.6 | 3.136 | 264.6 | 3.123 |
| 279.3 | 3.173 | 279.3 | 3.151 | 279.3 | 3.154 | 279.3 | 3.155 | 279.3 | 3.141 |
| 294.0 | 3.192 | 294.0 | 3.171 | 294.0 | 3.170 | 294.0 | 3.179 | 294.0 | 3.160 |
| 308.7 | 3.214 | 308.7 | 3.192 | 308.7 | 3.189 | 308.7 | 3.197 | 308.7 | 3.184 |
| 323.4 | 3.234 | 323.4 | 3.215 | 323.4 | 3.208 | 323.4 | 3.222 | 323.4 | 3.209 |
| 338.1 | 3.250 | 338.1 | 3.233 | 338.1 | 3.227 | 338.1 | 3.237 | 338.1 | 3.228 |

This invention has been described herein in considerable detail in order to comply with the Patent Statutes and to provide those skilled in the art with the information needed to apply the novel principles and to construct and use such specialized components as are required. However, it is to be understood that the invention can be carried out by specifically different equipment and devices, and that various flexible catheter body, an outermost wall of the double walled tubular member being a polyamide and an inner wall of the double walled tubular member being polyethylene terephthalate, where the percentage by volume of the polyamide is in a range of from 20 to 80 percent and with the balance being polyethylene terephthalate, the double walled tubular member exhibiting a compliance factor of about 13 percent or less over a pressure range of from 8 atmospheres to 18 atmospheres; and (c) means affixing the double walled tubular member to said distal end of the said elongated flexible tubular member with the lumen being in fluid communication with a chamber defined by the double walled tubular member.

6. The expander member as in claim 5 wherein the polyamide is Nylon-12.

7. The expander member as in claim 5 wherein the burst strength of the double walled tubular member is in excess of 25 atmospheres.

8. The balloon catheter as in claim 5 wherein said double walled tubular member is heat treated to enhance conformance of the double walled tubular member to the elongated flexible tubular member following inflation by the inflation fluid and subsequent aspiration of the inflation fluid from said chamber.

9. A method of deploying a stent comprising:

(a) disposing a balloon expandable stent about an inflatable expander member, wherein the expander member comprises a double-walled, tubular member adapted for attachment to a distal end portion of an elongated, flexible catheter body, an outermost wall of the double-walled tubular member being polyamide and an inner wall of the double-walled tubular member being polyethylene terephthalate, wherein the percentage by weight of polyamide is in a range of from 20 to 80 percent and with the balance being polyethylene terephthalate, the double walled tubular member exhibiting a compliance factor of about 13 percent or less over a pressure range of from 8 atmospheres to 18 atmospheres;

(b) percutaneously advancing the stent expander member assembly to a treatment site;

(c) inflating the expander member to a pressure greater than or equal to 8 atmospheres to expand the stent at the treatment site.

10. The method of claim 9 wherein the stent is expanded to a diameter which is not greater than 110 percent of the expander member's diameter at 8 atmospheres.

11. A method of deploying a self-expanding stent comprising:

(a) delivering a self-expanding stent to a treatment site and allowing it to self-expand at least partially against a vessel wall;

(b) deploying an expander member within the expanded stent, wherein the expander member comprises a double-walled, tubular member adapted for attachment to a distal end portion of an elongated, flexible catheter body, an outermost wall of the double-walled tubular member being polyamide and an inner wall of the double-walled tubular member being polyethylene terephthalate, wherein the percentage by weight of polyamide is in a range of from 20 to 80 percent and with the balance being polyethylene terephthalate, the double walled tubular member exhibiting a compliance factor of about 13 percent or less over a pressure range of from 8 atmospheres to 18 atmospheres;

(c) expanding the expander member to push the self-expanding stent firmly against the vessel wall.

12. The method of claim 11 wherein the diameter of the self-expanding stent when firmly pushed against the vessel wall is not greater than 110 percent of the expander member's diameter at 8 atmospheres.

* * * * *